United States Patent [19]
Van Lier et al.

[11] Patent Number: 5,864,044
[45] Date of Patent: Jan. 26, 1999

[54] SYNTHESES OF TRISULFONATED PHTHALOCYANINES AND THEIR DERIVATATIVES USING BORON (111) SUBPHTHALOCYANINES AS INTERMEDIATES

[75] Inventors: Johannes E. Van Lier, North Hatley; Svetlana V. Kudrevich; Sandra Gilbert, both of Sherbrooke, all of Canada

[73] Assignee: Universite de Sherbrooke, Sherbrooke, Canada

[21] Appl. No.: 899,861

[22] Filed: Jul. 24, 1997

[51] Int. Cl.$^6$ .............................. C07F 5/02; C07D 209/04

[52] U.S. Cl. .............................. 548/405; 546/13; 548/110

[58] Field of Search ...................................... 540/145, 122, 540/121; 430/270; 514/183, 185; 604/4; 424/9, 1.1; 548/405; 546/13

[56] References Cited

PUBLICATIONS

Kabayashi et al. J. Amer. Chem. Soc., 112, pp. 9640–9641, 1990.
Kudrevich et al. J. Org. Chem 61, pp. 5706–5707, 1996.

*Primary Examiner*—Mukund J. Shah
*Assistant Examiner*—Pavanaram K. Sripada
*Attorney, Agent, or Firm*—Goudreau Gage Dubuc & Martineau Walker

[57] ABSTRACT

Disclosed herein are novel trisulfonated phathalocyanines, processes for making them and their derivatives. Also disclosed are key intermediates consisting of Boron(III) subphathalocyanines. Further disclosed are novel uses for various water soluble trisulfophathalocyanines, trisulfobenzonapthoporphyrazines and trisulfonated phathalocyanines. The new uses are directed to photsensitizers for the photodynamic therapy of cancer, the inactivation of viruses in stored blood, organic semiconductors, disk memory material or as materials for gas sensors. In the compounds of the present invention, the central metal atom may be Zn, Co(II), Ni or Cu(II).

7 Claims, No Drawings

SYNTHESES OF TRISULFONATED PHTHALOCYANINES AND THEIR DERIVATATIVES USING BORON (III) SUBPHTHALOCYANINES AS INTERMEDIATES

BACKGROUND OF THE INVENTION

Phthalocyanines (Pc's) and their symmetrically substituted derivatives have received extensive interest in the last decades since their special properties (e.g. electrical conductivity, electrochromism, mesophase formation and aggregation into monolayers of Langmuir-Blodgett type) make them interesting substrates for new materials. Much less is known about the unsymmetrical derivatives of Pc which are expected to maintain additional facilities in areas like photodynamic therapy of cancer (PDT), photoinactivation of viruses in stored blood products and nonlinear optics.

The reason for the limited use of this type of compounds is mostly attributed to the difficulty of isolating the desired products from the statistically condensed mixture of two or more different phthalonitrile (diiminoisoindoline) derivatives. Complexity of such mixtures requires time-consuming chromatographical separation procedures and the yield of the desired products is usually very low. Therefore, efficient synthetic routes to each isomer are required. In this context three methods for the preparation of mono- and disubstituted lipophilic Pc's and their analogs are noteworthy: condensation of an iminoisoindoline derivatives either with 1,3,3-trichloroisoindoline, with another sterically crowded diiminoisoindoline or with 1,3-bis((3'-imino-1'-isoindolinydene) amino)-1,2,4-triazole (or its metal complex). None of these methods have been applied to the synthesis of Pc's featuring hydrophilic substituents, specifically sulfo groups, on the benzo rings. Meanwhile, designing the synthetic ways leading to water soluble and amphiphilic Pc's and their analogs, carrying well defined substituents, remains a challenge. Due to their water solubility and/or ease of formulation, these compounds are particularly sought after as photosensitizers for medical application. Some amphiphilic Pc's, envisioned for this application, such as metal free mono(tert-butyl) trisulfoPc and its zinc complex, could not be obtained using conventional condensation of two different precursors. We have recently reported the method for preparing monosulfonated Pc's and their derivatives via the Meerwein reaction, affording the definite positional isomers without chromatographical separation of polysulfonated mixtures. However, di- and trisulfonated Pc's cannot be obtained using this synthetic route.

There was surprisingly discovered an alternative procedure for the preparation of unsymmetrical Pc's with identical substituents on three of the benzene units and a different substituent on the fourth one. Preorganization of three phthalonitrile units as a subphthalocyanine (SubPc) of boron (III) and subsequent conversion into a Pc macrocycle via reaction with various substituted diiminoisoindolines, has proven to be an efficient way of obtaining unsymmetrical Pc's containing different lipophilic substituents, such as alkyl-, alkoxy-, alkylthio-, nitro- and crown ester groups. To our knowledge, this method was never applied for the preparation of water soluble Pc's, and SubPc's substituted with hydrophilic moieties in benzo rings are not known in the art.

Compared to Pc's, SubPc's—i.e. the lower homologues of Pc composed of three diiminoisoindoline units have traditionally been ignored because of difficulties related to their purification (b,e). Meller and Ossko reported the synthesis of boron(III) SubPc's with an axial halogen, SubPcB (X), where X=F, Cl, already in 1972. In their experiments, SubPc's were formed in the reaction of $BF_3$, $BCl_3$ or $PhBCl_2$ with phthalonitrile in boiling 1-chloronaphthalene. Subsequently it was shown that this procedure results in the formation of many secondary products, consisting of peripherally halogenated products, which complicate separation and purification of the desired products. These secondary reactions concern electrophilic substitution of free halogen, generated from $BX_3$ (X=F, Cl) or $PhBCl_2$ with the macrocycle, catalysed by unreacted $BX_3$.

Formation of unsubstituted and tris(tert-butyl) substituted SubPc's with an axial bromine, SubPcB(Br), was also described. These compounds were obtained by reaction of bromophenylboranes ($Ph_2BBr$ or $PhBBr_2$) and appropriate phthalonitrile in 1-chloronaphthalene. However, further attempts to repeat the synthesis of tert-$Bu_3$SubPcB(Br) yielded a product, which was identified as tert-$Bu_3$SubPcB (Ph) containing an axial phenyl group.

The present invention relates to the synthesis of the bromoboron(III) tri(4-chlorosulfonyl)SubPc 1, hydroxyboron(III) tri(4-sulfo)SubPc tripyridinium salt 2 and hydroxyboron(III) tri(4-alkylsulfamoyl)SubPc or hydroxyboron(III) tri(4-phenylsulfamoyl)SubPc type of 3, which served as precursors for the preparation of a wide range of unsymmetrical metal free Pc's, benzonaphthoporphyrazines (BNP's), and Pc aza-analogs (azaPc's), containing three sulfo- or sulfamoyl groups per molecule (Scheme 1).

Reactions of SubPc's with the diiminoisoindoline derivatives were accomplished at different temperatures depending on the reactivity of the latter compounds, using DMSO or a mixture DMSO—1-chloronaphthalene 2:1 as solvent Synthesized Pc's and their derivatives were purified by reprecipitation from different solvents depending on the type of substituents and, therefore, solubility.

Further metallation of the metal free compounds with divalent metals was accomplished using appropriate metal salts in methanol and/or DMF.

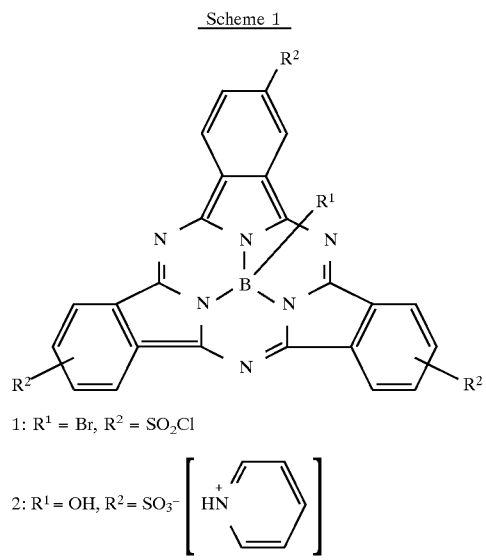

Scheme 1

1: $R^1$ = Br, $R^2$ = $SO_2Cl$

2: $R^1$ = OH, $R^2$ = $SO_3^-$ [ $HN^+$ (pyridine) ]

3: $R^1$ = OH, $R^2$ = $SO_2NHR^3$ or $SO_2NR^4R^5$, where $R^3$, $R^4$, $R^5$ is alkyl, hydroxyalkyl or Ph

Scheme 2
Group 1. Phthalocyanines

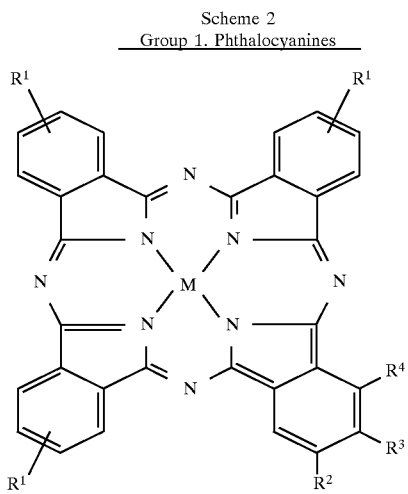

4–27
For
4–15: $R^1 = SO_3H$, for 16–27: $R^1 = SO_2NHR^5$,
  $SO_2NR^6R^7$, where
  $R^5$, $R^6$, $R^7$ is alkyl, hydroxyalkyl or Ph.

4,16: $R^4 = R^3 = R^2 = H$, (a)$M = HH$, (b)$M = Zn$,
  (c)$M = Co(II)$,
  (d)$M = Ni$, (e)$M = Cu(II)$.

5,17: $R^2 = t$-Bu, $R^3 = R^4 = H$, (a)$M = HH$, (b)$M = Zn$,
  (c)$M = Co$, (d)$M = Ni$, (e)$M = Cu$.

6,18: $R^2 = $ neopenthoxy, $R^3 = R^4 = H$, (a)$M = HH$,
  (b) $M = Zn$,
  (c)$M = Co$, (d)$M = Ni$, (e)$M = Cu$.

7,19: $R^4 = $ neopenthoxy, $R^2 = R^3 = H$, (a)$M = HH$,
  (b)$M = Zn$, (c)$M = Co$,
  (d)$M = Ni$, (e)$M = Cu$.

8,20: $R^4 = NO_2$, $R^2 = R^3 = H$, (a)$M = HH$,
  (b)$M = Zn$, (c)$M = Co$,
  (d)$M = Ni$, (e)$M = Cu$.

9,21: $R^2 = NO_2$, $R^3 = R^4 = H$, (a)$M = HH$,
  (b)$M = Zn$, (c)$M = Co$,
  (d)$M = Ni$, (e)$M = Cu$.

10,22: $R^4 = NH_2$, $R^2 = R^3 = H$, (a)$M = HH$,
  (b)$M = Zn$, (c)$M = Co$,
  (d)$M = Ni$, (e)$M = Cu$.

11,23: $R^2 = NH_2$, $R^3 = R^4 = H$, (a)$M = HH$,
  (b)$M = Zn$, (c)$M = Co$,
  (d)$M = Ni$, (e)$M = Cu$.

12,24: $R^4 = NHCOCH_3$, $R^2 = R^3 = H$,
  (a)$M = HH$, (b)$M = Zn$, (c)$M = Co$,
  (d)$M = Ni$, (e)$M = Cu$.

13,25: $R^2 = NHCOCH_3$, $R^3 = R^4 = H$,
  (a)$M = HH$, (b)$M = Zn$, (c)$M = Co$,
  (d)$M = Ni$, (e)$M = Cu$.

14,26: $R^2 = NHCOR^8$, where $R^8$ is alkyl or hydroxyalkyl,
  $R^3 = R^4 = H$ or alkyl or hydroxyalkyl,
  (a)$M = HH$, (b)$M = Zn$, (c)$M = Co$,
  (d)$M = Ni$, (e)$M = Cu$.

15,27: $R^2 = R^3 = $ alkyl or hydroxyalkyl or $OR^9$,
  where $R^9$ is alkyl or hydroxyalkyl,
  $R^4 = H$,
  (a)$M = HH$, (b)$M = Zn$, (c)$M = Co$,
  (d)$M = Ni$, (e)$M = Cu$.

Scheme 3
Group 2. Benzonaphthoporphyrazines

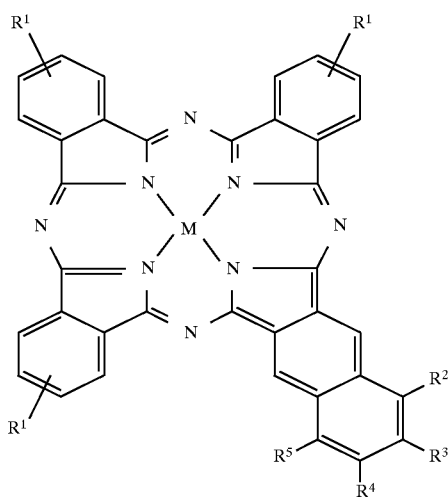

28–37
For
28–32: $R^1 = SO_3H$, for 33–37: $R^1 = SO_2NHR^6$ or
  $SO_2NR^7R^8$, where
  $R^6$, $R^7$, $R^8$ is alkyl, hydroxyalkyl or Ph.

28,33: $R^2$–$R^5 = H$, alkyl or hydroxyalkyl,
  (a)$M = HH$, (b)$M = Zn$, (c)$M = Co$,
  (d)$M = Ni$, (e)$M = Cu$.

29,34: $R^3 = t$-Bu, $R^2 = R^4 = R^5 = H$,
  (a)$M = HH$, (b)$M = Zn$, (c)$M = Co$,
  (d)$M = Ni$, (e)$M = Cu$.

30,35: $R^2 = NO_2$, $R^3$–$R^5 = H$,
  (a)$M = HH$, (b)$M = Zn$, (c)$M = Co$,
  (d)$M = Ni$, (e)$M = Cu$.

31,36: $R^2 = NH_2$, $R^3$–$R^5 = H$,
  (a)$M = HH$, (b)$M = Zn$, (c)$M = Co$,
  (d)$M = Ni$, (e)$M = Cu$.

32,37: $R^3$, $R^4 = $ 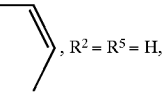 , $R^2 = R^5 = H$, (a)$M = HH$, (b)$M = Zn$, (c)$M = Co$,
  (d)$M = Ni$, (e)$M = Cu$.

Scheme 4
Group 3. Phthalocyanine Aza-analogs

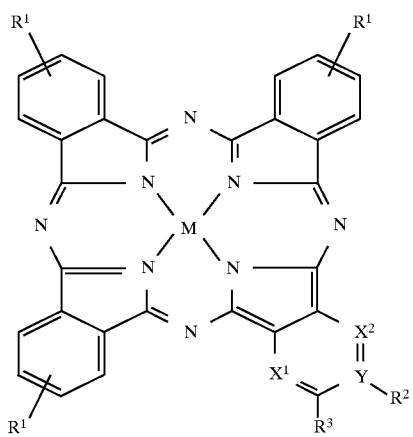

-continued
Scheme 4
Group 3. Phthalocyanine Aza-analogs

38–46, 46*, 46**, 47–55, 55*, 55**

For
38–46, 46*, 46**: $R^1 = SO_3H$; for 47–55, 55*, 55**:
$R^1 = SO_2NHR^4$ or $SO_2NR^5R^6$, where
$R^4$, $R^5$, $R^6$ is alkyl, hydroxyalkyl or Ph.

For 38–55, 46*, 46**, 55*, 55**:
(a)M = HH, (b)M = Zn, (c)M = Co, (d)M = Ni, (e)M = Cu.

38–47: $X^1 = N$, $X^2 = CH$, $Y = C$, $R^2 = R^3 = H$,
alkyl or hydroxyalkyl.

39,48: $Y = N$, $X^1 = X^2 = CH$, $R^2 = R^3 = H$.

For 40–46, 46*, 46**, 49–55, 55*, 55**:
$X^1 = X^2 = N$, $Y = C$.

40,49: $R^2 = R^3 = H$.
41,50: $R^2$ and/or $R^3$ = alkyl or hydroxyalkyl.

42,51: $R^2 = R^3 = Ph$ 43,52: $R^2$, $R^3$ = 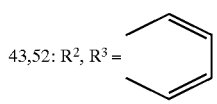

44,53: $R^2$, $R^3$ = 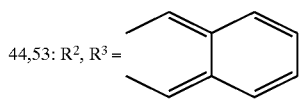

45,54: $R^2$, $R^3$ = 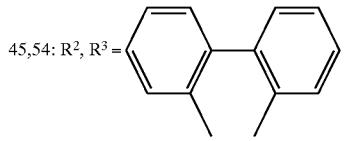

46,55: $R^2 R^3$ = 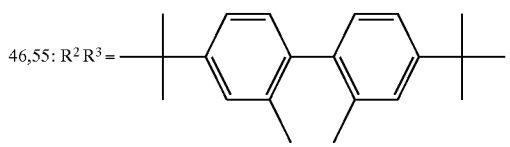

46*,55*: $R^2$, $R^3$ = 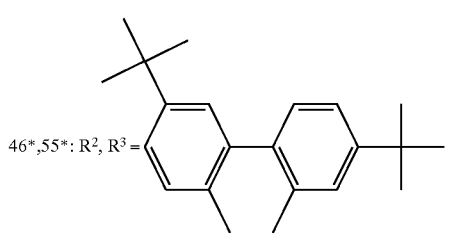

46,55: $R^2$, $R^3$ = 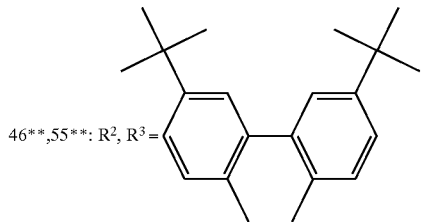

Varying substituents on the benzo rings of diiminoisoindoline allows for fine tuning of the long-wave absorption maxima of Pc's. Increasing the lipophilic part of the molecule which always contains three sulfo groups on its hydrophilic part, e.g. series 14, 15 (Group 1, Scheme 2), 29, 32 (Group 2, Scheme 3) or 42, 44–46 (Group 3, Scheme 4), and introducing additional N-atoms into the benzo rings of Pc's (Group 3) allows for control of the solubility of the resulting complexes in a vast range of organic solvents and in water at different pH values.

Therefore, the sulfonated derivatives of boron(II) SubPc 1–3 present the universal synthones for preparing unsymmetrical Pc's and their analogs which absorb in the range 600–800 nm (principal absorption maximum) and which possess different solubility—from water soluble through amphiphilic to lipophilic.

Water soluble and amphiphilic Pc's, BNP's and azaPc's 4–5 (Scheme 2), 28–32 (Scheme 3), and 38–46 (Scheme 4), prepared by reaction of 2 with various diiminoisoindolines, can be used as photosensitizing agents in PDT of cancer, for inactivation of viruses in stored blood products, and as materials for gas sensors.

The lipophilic derivatives 16–17 (Scheme 2), 33–37 (Scheme 3), 47–55 (Scheme 4), synthesized from sulfamoyl substituted SubPc's type of 3, can be useful as materials for organic semiconductors and disk memory.

Scheme 5

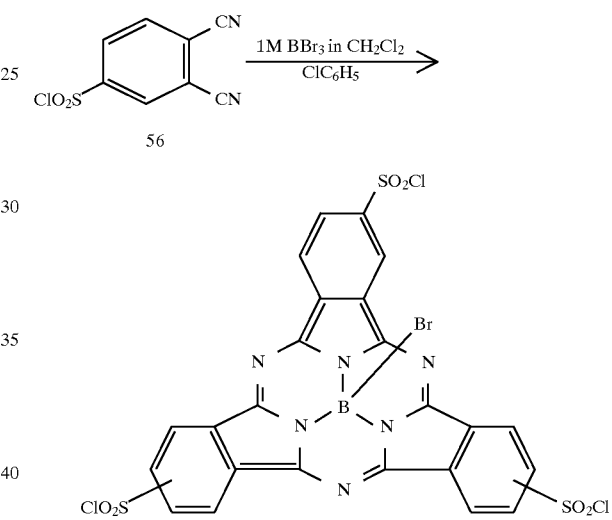

DETAILED DESCRIPTION OF THE INVENTION

To synthesize tri(4-chlorosulfonyl)SubPcB(Br) 1 from 4-chlorosulfonyl-phthalonitrile 56, we used a commercially available 1M solution of $BBr_3$ in dichloromethane. With this reagent we excluded the possibility of producing halogenated by-products (Scheme 5). The reaction was accomplished in 1-chlorobenzene, which has a lower boiling point as compared to 1-chloro-naphthalene, i.e. the solvent previously used for such cyclotrimerization. In contrast to the unsubstituted analog which was synthesized at much higher temperatures (e.g. at reflux temperature of 1-chloronaphthalene), the reaction leading to 1 already started at room temperature and was accomplished in 1 hour at 40° C. 1Chlorobenzene was easily evaporated at reduced pressure, leaving product 1 as a dark purple solid. Compound 1 was obtained in high yield (>60%) and characterized by FAB mass, UV-vis and IR spectroscopy data which are in accordance with the assigned structure. It is soluble in organic solvents (such as chloroform, toluene, methanol). The chlorosulfonyl groups of 1 are susceptible to rapid hydrolysis accompanied by destruction of the macrocycle, if the compound is left exposed to the atmospheric air.

However, if stored in a hermetically sealed container and shielded from light, the sulfonyl chloride 1 remains unchanged for months. Due to its unstability, we did not attempt chromatographical purification and used the material directly in the next step of the reaction sequence. As such, compound 1 cannot be used as precursor to prepare unsymmetrical Pc's since the chlorosulfonyl moieties may react with the imino groups of diiminoisoindolines. Thus, the sulfonyl chloride 1 has to be converted to the sulfoacid derivative.

Our attempts to hydrolyse 1 in concentrated or diluted HCl, as well as in diluted aqueous solution of NaOH or ammonia lead to destruction of the boron SubPc macrocycle. To circumvent this problem, we developed conditions to stabilize the SubPc, involving hydrolysis in a mixture of water/pyridine (2:1) (Scheme 6). Compound 1 was simply dissolved in this mixture, and the solution was stirred for 12 hours at room temperature. Then, upon evaporation of the solvent under reduced pressure, the product was reprecipitated from acetone affording the pyridinium salt 2 as golden purple crystals in 60% yield. Compound 2 was fully characterized by combustion analysis and spectroscopic data. Compound 2 is soluble in water, DMF, DMSO and methanol. The UV-vis spectrum of 2 features a sharp absorption maximum at 569 nm, which is characteristic for SubPc's. HPLC analysis of aqueous solution of the salt 2 revealed a single peak with $t_R$ 10 min, which is similar to the $t_R$ of tetrasulfonated PcM in this system.

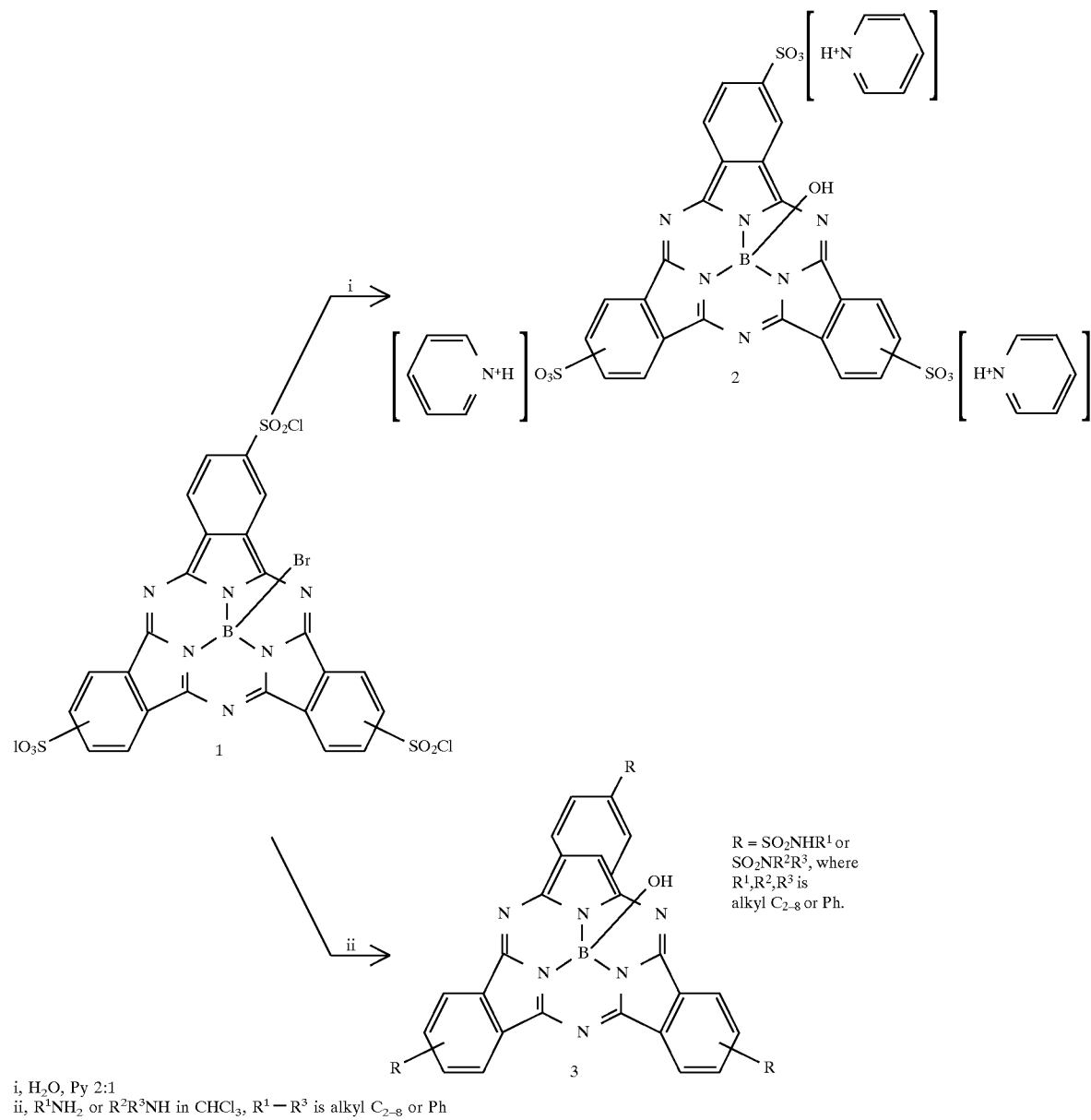

i, H$_2$O, Py 2:1
ii, R$^1$NH$_2$ or R$^2$R$^3$NH in CHCl$_3$, R$^1$—R$^3$ is alkyl C$_{2-8}$ or Ph Alkyl- and phenylsulfonamides 3 were obtained by treatment of the chloroform solution of 1 with appropriate primary or secondary amines, followed by chromatographical purification of the product (Scheme 5).

1,3-Diiminoisoindoline derivatives 57–82 were obtained by treatment of the corresponding o-dinitriles with sodium methylate and ammonia in methanol. o-Dinitriles, if not commercially available, were prepared by previously described methods. 1,3-Diiminoisoindolines of Group 1 were obtained from substituted phthalonitriles: 57—from phthalonitrile, 58—from 4-tert-butylphthalonitrile, 59 and 60—from 4-neopenthoxyphthalonitrile and 3-neopenthoxyphthalonitrile, respectively, 61 and 62—from 3- and 4-nitrophthalonitrile, respectively, 63, 64 and 65—from 3- and 4-acetamidophthalonitrile and corresponding 4-carboxamidophthalonitriles. 66—from 3,4-dialkoxyphthalonitriles. 1,3-Diiminoisoindolines of Group 2 were prepared from substituted 2,3-dicyanonaphthalenes: 67—from 2,3-dicyanonaphthalene, 68—from 6-tert-butyl-2,3-dicyanonaphthalene, 69—from 2,3-dicyano-5-nitronaphthalene, 70—from 2,3-dicyanoanthracene. 1,3-Diiminoisoindolines of Group 3 were synthesized from corresponding heterocyclic o-dinitriles: 71—from 2,3-dicyanopyridine, 72—from 3,4-dicyanopyridine, 73—from 2,3-dicyanopyrazine, 75—from 5,6-diphenyl-2,3-dicyanopyrazine, 76—from 2,3-dicyanoquinoxaline, 77—from 2,3-dicyanobenzoquinoxaline, 78-from5,6-(9,10-phenanthro)-2,3-dicyanopyrazine, 79, 79* and 79**—from 5,6-[2,7-di-tert-butyl-(9,10-phenanthro)]-2,3-dicyanopyrazine, 5,6-[2,6-di-tert-butyl-(9,10-phenanthro)]-2,3-dicyanopyrazine and 5,6-[3,6-di-tert-butyl-(9,10-phenanthro)]-2,3-dicyanopyrazine, respectively.

All compounds 57–79, 79*, 79** were used for further syntheses as crude products obtained upon evaporation of methanol from the reaction mixture, without further purification.

The reactions of 2 with diiminoisoindoline derivatives (Schemes 7, 8, 9) were accomplished at low temperatures as compared to other similar ring expansion reactions. Thus, compounds 57 and 58 react with 2 at room temperature. Using pure, dry DMSO as a solvent for the reactions with the tripyridinium salt 2, we obtained all desired Pc's in good yields (up to 50%).

The reactions of the more lipophilic tri (alkylsulfonamido)- and tri(phenylsulfonamido)SubPc's (type 3) were performed in a mixture of DMSO and 1-chloronaphthalene 2:1.

The maximum temperature used for all the reactions of 2 and 3 was 70° C. Under these conditions we obtained the desired unsymmetrical Pc's 46, 46*, 46**,47–55, 55*, 55**, whereas excess of the diiminoisoindoline derivatives did not result in formation of the corresponding, undesired, symmetrical, metal-free Pc derivatives.

Completion of the ring expansion reaction was determined spectro-photometrically: the absorption bands, characteristic for the metal-free Pc's, BNP's and azaPc's (around 650–700 nm), gradually increase during the course of the reaction, whereas the Q-band of boron SubPc (around 570 nm, depending on the solvent) gradually disappears.

The sulfoPc tripyridinium salts, obtained from 2, were precipitated from DMSO upon the addition of methanol and/or chloroform, and isolated by simple filtration to yield fairly pure compounds. Multiple redissolvation of the pyridinium salts in water, followed by reprecipitation with HCl, gave analytical samples of the corresponding sulfoacids 4–15, 28–32 and 38–46, 46*, 46**. HPLC analysis of the latter compounds showed the presence of only one fraction, consisting of three more or less resolved peaks of the type isomers, in each case, with $t_R$ around 20 min, corresponding to trisulfonated Pc's.

The sulfonamides 16–27, 33–37 and 47–55, 55*, 55**, obtained from 3 (Schemes 7, 8, 9), were isolated from the DMSO—1-chloronaphthalene medium upon addition of water and then purified by reprecipitation from the organic solvents or chromatographically (depending on substituents).

Monoamino Pc's 10, 11, 22, 23 and monoamino BNP's 31, 36 were obtained by deprotection of the corresponding acetamides 12, 13, 24, 26 in HCl or by reduction of the corresponding nitrocompounds 8, 9, 20, 21 and 30, 35 with sodium sulfide nonahydrate.

Scheme 7
Group 1.
Phthalocyanines

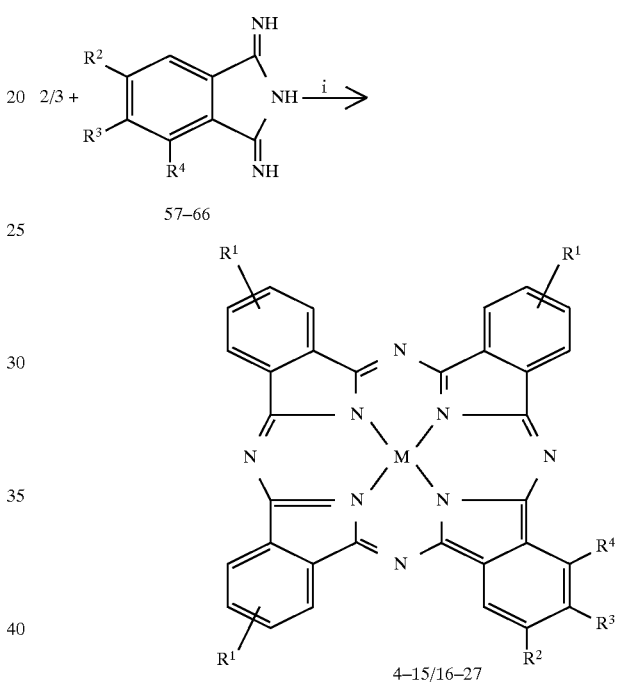

57–66

4–15/16–27

For 4–15: $R^1$ = $SO_3H$; for 16–27: $R^1$ = $SO_2NHR^5$, $SO_2NR^6R^7$, where $R^5,R^6,R^7$ is alkyl, hydroxyalkyl or Ph.

For 4–27: (a) M = HH, (b) M = Zn, (c) M = Co(II), (d) M = Ni, (e) M = Cu.

4,16,57: $R^2$ = $R^3$ = $R^4$ = H.

5,17,58: $R^2$ = t-Bu, $R^3$ = $R^4$ = H.

6,18,59: $R^2$ = neopenthoxy, $R^3$ = $R^4$ = H.

7,19,60: $R^4$ = neopenthoxy, $R^2$ = $R^3$ = H.

8,20,61: $R^4$ = $NO_2$, $R^2$ = $R^3$ = H.

9,21,62: $R^2$ = $NO_2$, $R^3$ = $R^4$ = H.

10–22: $R^4$ = $NH_2$, $R^2$ = $R^3$ = H.

11,23: $R^2$ = $NH_2$, $R^3$ = $R^4$ = H, (a) M = HH, (b) M = Zn, (c) M = Co, (d) M = Ni, (e) M = Cu.

12,24,63: $R^4$ = $NHCOCH_3$, $R^2$ = $R^3$ = H.

13,25,64: $R^2$ = $NHCOCH_3$, $R^3$ = $R^4$ = H.

14,26,65: $R^2$ = $NHCOR^8$, where $R^8$ is alkyl or hydroxyalkyl, $R^3$ = $R^4$ = H or alkyl or hydroxyalkyl.

Scheme 7
Group 1.
Phthalocyanines 15,27,66: $R^2 = R^3$ = alkyl or hydroxyalkyl or $OR^9$, where $R^9$ is alkyl or hydroxyalkyl, $R^4 = H$.

i, for 4–15
DMSO; for 16–27: DMSO, 1-chloronaphthalene 2:1

Scheme 8
Group 2.
Benzonaphthoporphyrazines

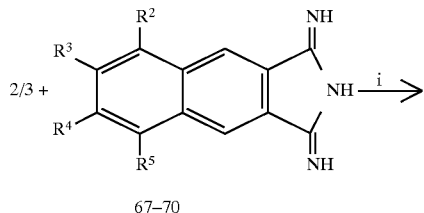

67–70

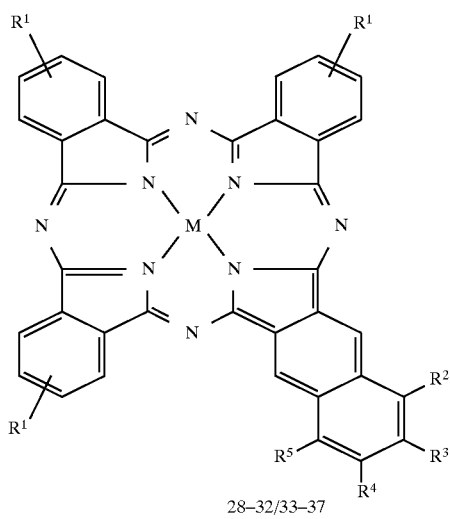

28–32/33–37

For 28–32: $R^1 = SO_3H$; for 33–37: $R^1 = SO_2NHR^6$ or $SO_2NR^7R^8$, where $R^6, R^7, R^8$ is alkyl, hydroxyalkyl or Ph.

For 28–37: (a) M = HH, (b) M = Zn, (c) M = Co(II), (d) M = Ni, (e) M = Cu.

28,33,67: $R^2-R^5$ = H, alkyl or hydroxyalkyl 29,34,68: $R^3$ = t-Bu, $R^2 = R^4 = R^5$ = H.

30,35,69: $R^2 = NO_2$, $R^3-R^5$ = H 31,36: $R^2 = NH_2$, $R^3-R^5$ = H.

32,37,70: $R^3, R^4$ = [cyclohexene ring], $R^2 = R^5$ = H.

i, for 28–32
DMSO; for 33–37: DMSO, 1-chloronaphthalene 2:1

Scheme 9
Group 3.
Phthalocyanine Aza-analogs

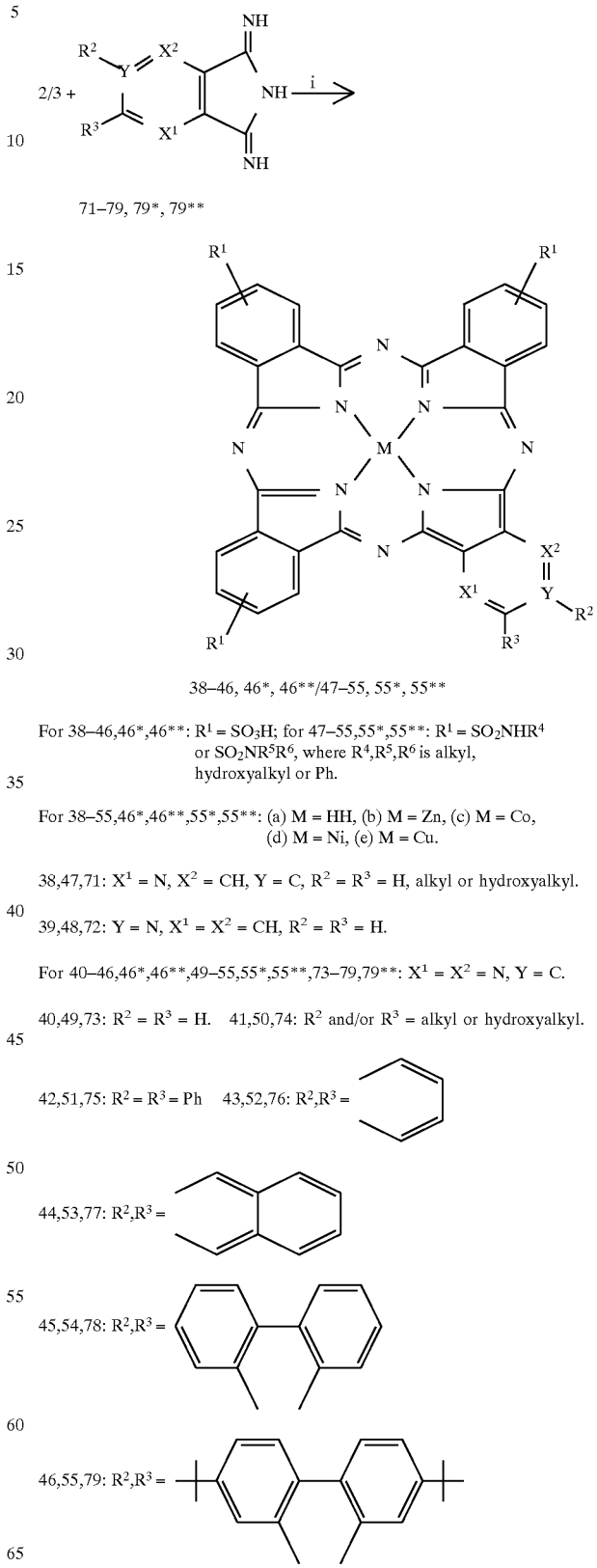

71–79, 79*, 79**

38–46, 46*, 46**/47–55, 55*, 55**

For 38–46,46*,46**: $R^1 = SO_3H$; for 47–55,55*,55**: $R^1 = SO_2NHR^4$ or $SO_2NR^5R^6$, where $R^4, R^5, R^6$ is alkyl, hydroxyalkyl or Ph.

For 38–55,46*,46**,55*,55**: (a) M = HH, (b) M = Zn, (c) M = Co, (d) M = Ni, (e) M = Cu.

38,47,71: $X^1$ = N, $X^2$ = CH, Y = C, $R^2 = R^3$ = H, alkyl or hydroxyalkyl.

39,48,72: Y = N, $X^1 = X^2$ = CH, $R^2 = R^3$ = H.

For 40–46,46*,46**,49–55,55*,55,73–79,79: $X^1 = X^2$ = N, Y = C.

40,49,73: $R^2 = R^3$ = H.   41,50,74: $R^2$ and/or $R^3$ = alkyl or hydroxyalkyl.

42,51,75: $R^2 = R^3$ = Ph   43,52,76: $R^2, R^3$ = [cyclohexene]

44,53,77: $R^2, R^3$ = [naphthalene]

45,54,78: $R^2, R^3$ = [dimethylbiphenyl]

46,55,79: $R^2, R^3$ = [tetramethylbiphenyl]

-continued
Scheme 9
Group 3.
Phthalocyanine Aza-analogs

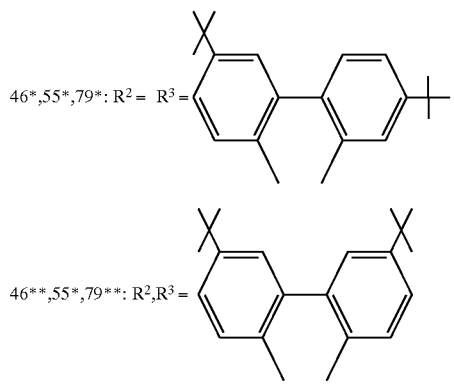

46*,55*,79*: R² = R³ =

46,55,79**: R²,R³ = i, for 38–46,46*,46**: DMSO;
for 47–55,55*,55**: DMSO, 1-chloronaphthalene, 2:1

The synthesized monoamino Pc's, BNP's and azaPc's can be bound to the activated carboxyl compounds or isothiocyanates, such as rhodamine or fluorescein isothiocyanates of biological importance, such as rhodamine or fluorescein isothiocyanates, biotin succinimidyl ester, acridine carbonyl chloride or other DNA intercalating agents featuring an appropriate attachment group.

All metal free Pc derivatives thus prepared were readily metallated with Zn, Cu(II), Co(II) or Ni, using zinc acetate dihydrate, copper(II) chloride, cobalt(II) chloride or nickel acetate in methanol and/or DMF.

The following specific examples illustrate, but do not limit the invention. FAB-mass spectra were obtained on a mass spectrometer from the Department of Chemistry, Université Laval (Quebec, Quebec). IR spectra were taken on a UV-vis spectra and were recorded with a Hitachi U-2000 spectrophotometer.

Preparative chromatography was done on 70–230 mesh silica gel (Aldrich). TLC was performed on 0.25 mm thick POLYGRAM SIL G/UV$_{254}$ plates (Macherey-Nagel, Germany). Analytical HPLC was conducted on a 0.94×25 cm column (CSC, Montreal) packed with ODS-2, C-18 reversed-phase particles and operated with a linear gradient from 100% aq. sodium phosphate buffer (pH 7) to 100% methanol over a period of 30 minutes, followed by isocratic elution with 100% methanol for 10 minutes, at 1.5 ml/min. Eluted Pc's, NBP's and azaPc's were detected by their absorbance at 650–700 nm, boron SubPc's—at 569 nm.

4-tert-Butylphthalonitrile and 4-nitrophthalonitrile were purchased from TCI America, 3-nitrophthalonitrile, 2,3-dicyanopyridine, 3,4-dicyanopyridine, 2,3-dicyanopyrazine and 2,3-dicyanonaphthalene were obtained from Aldrich.

Satisfactory results of elemental analysis for compounds 1–3, 5, 5b, 17, 29 and 42, mentioned below, were obtained.

EXAMPLE 1

Bromoboron(III) Tri(4-chlorosulfonyl) subphthalocyanine 1 (Scheme 5)

Compound 56 (2 g, 8.83 mmol) was dissolved in anhydrous 1-chlorobenzene (5 ml). A 5 ml solution of 1M BBr$_3$ in dichloromethane (1.26 g, 5 mmol of BBr$_3$) was added dropwise. The mixture, which immediately became dark purple, was stirred for 15 minutes at room temperature, and was then heated to 40° C. and maintained at this temperature for 2 hours. After cooling to room temperature, the solvent was evaporated under reduced pressure. The crude compound 1, soluble in CHCl$_3$, toluene, CCl$_4$ (magenta coloured solutions) was used without further purification in the next step.

FAB-MS, m/e: 677 (M$^+$–BBr), 226 ((4-chlorosulfonyl) phthalonitrile).
$\lambda_{max}$(CHCl$_3$), nm: 569, 226. IR, cm$^{-1}$: 1475–1350s, 1220–1175s (S=O, sulfonyl chloride).

EXAMPLE 2

Hydroxyboron(III) Tri(4-sulfo)subphthalocyanine, Tripyridinium Salt 2 (Scheme 6)

2.2 g of crude compound 1 was dissolved in a mixture of 30 ml pyridine and 60 ml H$_2$O. This solution was shielded from light and stirred at room temperature for 12 hours. The solvent was then evaporated under reduced pressure. The residue (dark purple solid) was redissolved in a minimal amount of water (about 10 ml). This purple solution was filtered (no residue), and poured into 300 ml of cold acetone. Precipitated dark purple slurry was separated by centrifugation. Slightly pink supernatant was discarded, the pellet was washed with acetone and dried in vacuo (1 mm Hg, 30°–40° C.) for 6 h. Compound 2 (1.75 g, 60% yield based on 2 pentahydrate, according to combustion analysis data, and starting compound 56) was obtained as golden purple crystals. Compound 2 is soluble in water, DMSO and methanol (magenta coloured, light sensitive solutions).

FAB-MS, m/e (sulfo-acid form): 625 (M$^+$–BOH), 206.5 (4-sulfophthalo-nitrile). $\lambda_{max}$[H$_2$O], nm (log ε): 569(4.85), 515(sh), 226(4.4). IR, cm$^{-1}$: 1135–1187s, 1036–1029s, 676–644s (S=O). HPLC analysis: 1 peak, $t_R$ 10 min.

EXAMPLE 3

Hydroxyboron(III) Tri(4-phenylsulfonamido) subphthalocyanine 3 (Scheme 6)

Compound 1 (0.4 g) was dissolved in 30 ml of CHCl$_3$ and shielded from light. After cooling the solution in an ice bath, 0.7 g of aniline was added and the mixture was stirred at 0° C. for 0.5 h, then brought to room temp. The resulting dark purple solution contained some precipitate. Chloroform was evaporated, 10 ml of water were added to the residue, and sulfonamide was extracted with chloroform. Chromatographical purification using a mixture of chloroform/THF (3:1) as eluant afforded 0.305 g (69%) of compound 3. $\lambda_{max}$(DMSO), nm: 566, 225.

EXAMPLE 4

Mono(4-tert-butyl)tri(4-sulfo)phthalocyanine 5 (Scheme 7. Group 1. Phthalocyanines)

A solution of 2 (0.2 g, 0.2 mmol) in 10 ml of anhydrous DMSO was added to a solution of 58 (0.4 g, 2 mmol) in 10 ml of anhydrous DMSO. The mixture was shielded from light and kept at room temp. for 1 h, then it was diluted with 75 ml of methanol and stirred at room temp. for another 2 h. The blue precipitate of phthalocyanine was filtered, extensively washed with methanol and dried. Then the blue solid was redissolved in a minimal amount of water and precipitated upon addition of concentrated HCl. The precipitate was filtered, washed with diluted HCl, aq. methanol and acetone and dried in vacuo (1 mm Hg, 100° C.) for 6 hours. 52 mg (32%) of compound 5 was obtained.

$\lambda_{max}$(aq. methanol), nm: 690, 656, 633, 340. HPLC analysis (detector 656 nm): three peaks corresponding to trisulfoPc fraction, $t_R$ 21–24 min.

EXAMPLE 5

Mono(6-tert-butyl-naphtho)-tri(4-sulfobenzo) porphyrazine 29 (Scheme 8. Group 2. Benzonaphthoporphyrazines)

A solution of 2 (0.2 g, 0.2 mmol) and 68 (0.5 g, 2 mmol) in 20 ml of anhydrous DMSO was shielded from light and kept at 70° C. for 7 days. The end of reaction was detected spectro-photometrically. A little chloroform was added to the resulting dark green solution, and the waxy precipitate was separated. This pyridinium salt was redissolved in methanol, precipitated with a few drops of chloroform and centrifuged. This procedure of reprecipitation was repeated until the UV-vis spectrum of the compound was constant. The corresponding sulfo-acid 29 was obtained from the pyridinium salt upon dissolvation of the latter in water and precipitation with conc. HCl, and purified similar to compound 5. 40 mg (23%) of 29 was obtained.
$\lambda_{max}$[methanol], nm: 728, 692, 656, 340. HPLC analysis (detector 692 nm): three peaks corresponding to trisulfoPc fraction, $t_R$ 21.5–25 min.

EXAMPLE 6

Mono(5,6-diphenyl-2,3-pyrazino)-tri(4-sulfobenzo) porphyrazine 42 (Scheme 8, Group 3, Phthalocyanine Aza-analogs) was obtained and purified similar to compound 29 starting with 2 (0.2 g, 0.2 mmol and 75 (0.564 g, 2 mmol. It took about 2 days for this reaction to be completed at 70° C. 80 mg (45%) of compound 42 was obtained.
$\lambda_{max}$[methanol], nm: 677,659,605, 382. HPLC analysis (detector 677 nm): three peaks corresponding to trisulfoPc fraction, $t_R$ 20–24 min.

EXAMPLE 7

Mono(4-tert-butyl)tri(4-phenylsulfamido) phthalocyanine 17 (Scheme 7)

A mixture of 3 (0.2 g, 0.23 mmol), 58 (0.462 g, 2.3 mmol), anhydrous 1-chloronaphthalene (1 ml) and anhydrous DMSO (2 ml) was heated at 60°–70° C. for 4 h. After cooling to room temperature, a few drops of water were added to the reaction mixture, and the precipitate was separated. Chromatographical purification on silica gel using chloroform and THF as eluants afforded 47 mg (19%) of compound 17.
$\lambda_{max}$[DMSO], nm: 689, 655, 633, 345.

EXAMPLE 8

Zinc mono(4-tert-butyl)-tri(4-sulfo)phthalocyanine 5b

Compound 5 (50 mg, $6 \cdot 10^{-5}$ mol) and zinc acetate dihydrate (13 mg, $6 \cdot 10^{-4}$ mol) were dissolved in 10 ml of dry DMF and stirred at 60° C. for 1 h. After cooling the reaction mixture to room temp. the solvent was evaporated under reduced pressure, the residue was dissolved in a minimal amount of water and precipitated upon addition of conc. HCl. The precipitate was isolated, washed with methanol, dried, then the procedure of reprecipitation was repeated to yield 43 mg (82%) of compound 5b.
$\lambda_{max}$(aq. methanol), nm: 676, 610, 571, 350. HPLC analysis (detector: 676 nm): three peaks corresponding to trisulfopc fraction, $t_R$ 21–24 min.

The embodiments of the invention in which an exclusive property or privilege is claimed are defined as follows:

1. A water-soluble intermediate compound consisting of a subphthalocyanine compound of the following formula:

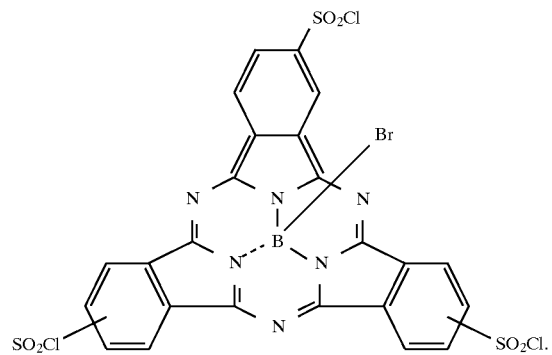

2. A method for the preparation of a compound of claim 1 comprising the steps preparing a solution of $BBr_3$ in dichloromethane mixed with 1-chlorobenzene and reacting therein a compound of the following formula:

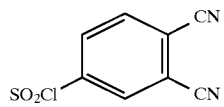

and recovering the compound of claim 1 via evaporating the 1-chlorobenzene under reduced pressure.

3. A water-soluble compound consisting of a salt of the compound of claim 1, said compound having the following formula:

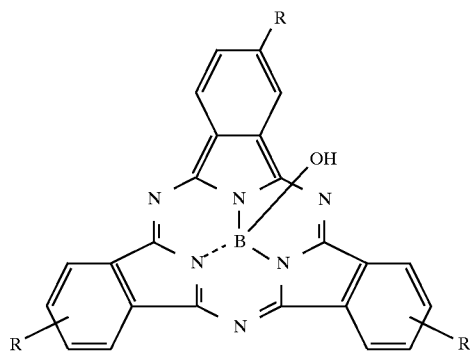

wherein R is

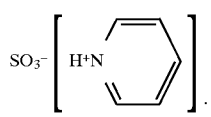

4. A method for the preparation of a compound of claim 3 comprising the steps hydrolyzing the compound of claim 1 in a solvent mixture consisting of water and pyridine and recovering the compound of claim 3.

5. The method of claim 4 wherein the ratio of water to pyridine is about 2:1.

6. A water-soluble compound consisting of a derivative of the compound of claim 1, said compound having the following formula:

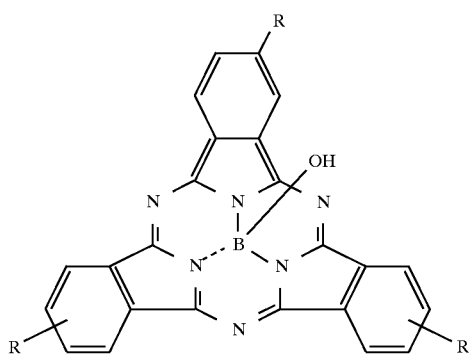

wherein

R is selected from the group consisting of $SO_2NHR^1$, $SO_2NHR^2R^3$, wherein $R^1$, $R^2$ and $R^3$ are selected from H, alkyl $C_{2-8}$ and Ph.

7. A method for the preparation of a compound of claim 5 comprising the steps placing the compound of claim 1 in a chloroform solution and treating said mixture with appropriate primary or secondary amines and recovering the product of claim 5 by purification.

* * * * *